United States Patent [19]
Thompson et al.

[11] Patent Number: 5,922,561
[45] Date of Patent: Jul. 13, 1999

[54] GENES ENCODING SIGNAL RECOGNITION PARTICLE OF *ASPERGILLUS NIGER*

[75] Inventors: Sheryl Ann Thompson; Debbie Sue Yaver, both of Davis, Calif.

[73] Assignee: Novo Nordisk Biotech, Inc., Davis, Calif.

[21] Appl. No.: 08/317,401

[22] Filed: Oct. 3, 1994

[51] Int. Cl.$^6$ .............................. C12P 21/02; C12N 1/00; C12N 1/15; C12N 5/10

[52] U.S. Cl. .................... 435/69.1; 435/243; 435/254.11; 435/254.3; 435/320.1; 435/325; 435/410; 536/23.74

[58] Field of Search .................................. 435/320.1, 325, 435/420, 243, 254.3, 254.11, 69.1, 70.1, 71.1; 536/23.1, 23.74

[56] References Cited

U.S. PATENT DOCUMENTS 5,426,043  6/1995  De Graaff et al. ...................... 435/197

OTHER PUBLICATIONS

Cheevadhanarak et al, Gene, vol. 108, pp. 151–155, 1991.
Krieg et al., Proc. Natl. Acad. Sci, vol. 83, pp. 8604–8608 (1986).
Kurzchalia et al., Nature, vol. 320 pp. 634–636 (1986).
Lindstrom et al., Plant Molecular Biol., vol. 23, pp. 1265–1272 (1993).
Bernstein et al., Nature, vol. 340, pp. 482–486 (1989).
Siegel et al., J. of Cell Biol., vol. 100, pp. 1913–1921 (1985).
Walter et al., Nature, vol. 299, pp. 691–698 (1982).
Perez–Perez et al., Biotechnology, vol. 12, pp. 178–180 (1994).
Sanford Simon, Current Opinion in Cell Biol., vol.5, pp. 581–585 (1993).
Hann et al., J. Cell Biol., vol. 109, No. 6, Pt.2, pp. 3223–3230 (1989).
Römisch et al., Nature, vol. 340, pp. 478–482 (1988).
Walter et al., Amer. Res. Cell Biol., vol. 2, pp. 499–516 (1986).
Ngo et al, The Protein Folding Problem and Tertiary Structure Prediction, 1994, Mertz et al (eds), Birkhauser, Boston, MA, pp. 433 and 492–495.

*Primary Examiner*—Terry McKelvey
*Attorney, Agent, or Firm*—Steve T. Zelson, Esq.; Robert Starnes

[57] ABSTRACT

The present invention relates to a nucleic acid construct containing a nucleic acid sequence encoding an element of a filamentous fungal signal recognition particle.

15 Claims, 7 Drawing Sheets

```
X   GRGKTTCKL-RHYQMRFKTALVCADTFRAGAFDQLKQNATKAKIPYYGSLTQTIDPAVVAAEGVAKFKKERF
    ||| |||| ||||| |||||||||||||||||||||||||||||||||||| |||||||| ||||||
    GIGKTTCTKLARHYQMRGKTALVCADTFRAGAFDQLKQNATKAKIPYYGSLTQTDPVVAAEGVEKFKKERF
X            10        20        30        40        50        60        70

E I I VDTSGRHKQEEELFTEMTQIQTA--VTPDQTILVLDSTIGQAAEAQSAAFKATADFGAIIITKTDGHA
    ||||||||||||||||||||||||||||   |||||||||||||||||| ||||||||||||| |||||||||
    E I I VDTSGRHKQEEELFTEMTQIQTAVTVTPDQTILVLDSTIGQAAEPQSAAFKATADFG-IIITKTDGHA
             80        90       100       110       120       130       140

AGGGAISAVAATHTPIIFIGTG      X
    ||||||| |||||||||||||
    AGGGAIS-VAATHTPIIFIGTG      X
             150       160
```

```
ATCGATTCAWCCATCTCGSTGSATCCTCCATTCGCTCTCTCCTGTCCTCTCTGCCACCTT  60

TCACGATTTCTGGCAGNAAGTGACGCATATTTTAATCTGTACATGCTTTAATTTGATTTA 120

CCTCCTTTCGACAAGAACTCCCCCGCCATGGTCCTTCAGGATCTCGGGCGGCGAATCAAC 180
                              M  V  L  Q  D  L  G  R  R  I  N

GCCGCCGTCAATGACCTGACTCGCTCTAACAATTTGGACGAGAAGGTGAGGATCAGCACT 240
 A  A  V  N  D  L  T  R  S  N  N  L  D  E  K ─────────────────

TTTCTCTCTGTCTGATGTATGTACTGACTGTTAGCAGGCCTTTGATGACATGATCAAAGA 300
────────────────────────────────── Q  A  F  D  D  M  I  K  E

GATCTGCGCCGCCTTGCTGTCCGCCGACGTCAACGTCCGCCTGGTCCAGTCCCTCCGCAA 360
 I  C  A  A  L  L  S  A  D  V  N  V  R  L  V  Q  S  L  R  K

ATCCATCAAGTCCAGCGTCAACTTTGCCTCTCTTCCTCCCGCCGTGAACAAGAAGCGTTT 420
 S  I  K  S  S  V  N  F  A  S  L  P  P  A  V  N  K  K  R  L

GATTCAGAAGGCCGTCTTCGATGAGCTGGTTTCCCTGGTTGATCCCCATGCGGAGCCATT 480
 I  Q  K  A  V  F  D  E  L  V  S  L  V  D  P  H  A  E  P  F

CCGTCCCAAGAAGGGCCGCTCCAACGTGATCATGTTCGTCGGTCTACAGGGTGCCGGTAA 540
 R  P  K  K  G  R  S  N  V  I  M  F  V  G  L  Q  G  A  G  K

AACCACCACCTGTACCAAGCTGGCCCGCCACTATCAGATGCGCGGCTTCAAGACCGCCCT 600
 T  T  T  C  T  K  L  A  R  H  Y  Q  M  R  G  F  K  T  A  L

CGTCTGTGCCGATACCTTCCGAGCTGGTGCTTTCGACCAGCTGAAACAGAATGCCACCAA 660
 V  C  A  D  T  F  R  A  G  A  F  D  Q  L  K  Q  N  A  T  K

GGCCAAGATCCCCTACTACGGTAGCCTGACGCAAACCGACCCCGCCATCGTGGCAGCCGA 720
 A  K  I  P  Y  Y  G  S  L  T  Q  T  D  P  A  I  V  A  A  E

GGGTGTGGCCAAGTTCAAGAAGGAGCGTTTCGAAATCATCATTGTCGATACCAGTGGTCG 780
 G  V  A  K  F  K  K  E  R  F  E  I  I  I  V  D  T  S  G  R

TCATAAGCAGGAAGAAGAGCTCTTCACCGAAATGACCCAGATTCAGACCGCCGTCACCCC 840
 H  K  Q  E  E  E  L  F  T  E  M  T  Q  I  Q  T  A  V  T  P

CGACCAGACCATCCTCGTCCTCGACAGCACCATCGGTCAGGCTGCCGAAGCCCAGTCCTC 900
 D  Q  T  I  L  V  L  D  S  T  I  G  Q  A  A  E  A  Q  S  S

CGCCTTCAAGGCCACCGCAGACTTCGGAGCCATCATCATCACCAAGACGGATGGTCACGC 960
 A  F  K  A  T  A  D  F  G  A  I  I  I  T  K  T  D  G  H  A
```

FIG. 2b

```
CGCAGGTGGTGGTGCTATTTCCGCCGTCGCCGCCACACACACTCCCATTATCTACCTCGG 1020
  A  G  G  G  A  I  S  A  V  A  A  T  H  T  P  I  I  Y  L  G

TACCGGTGAGCACTTGATGGACCTGGAACGTTTCGAGCCCAAGGCCTTCATCCAGAAGCT 1080
  T  G  E  H  L  M  D  L  E  R  F  E  P  K  A  F  I  Q  K  L

CCTGGGTATGGGTGATATGGCCGGACTGGTAGAGCACGTACAAGCCGTGACCAAGGACTC 1140
  L  G  M  G  D  M  A  G  L  V  E  H  V  Q  A  V  T  K  D  S

GGCCTCCGCCAAGGAAACATACAAGCACATCTCAGAAGGTATCTACACGCTGCGCGACTT 1200
  A  S  A  K  E  T  Y  K  H  I  S  E  G  I  Y  T  L  R  D  F

CCGCGAGAACATCACCTCCATCATGAAGATGGGTCCTCTCTCCAAGCTCTCCGGCATGAT 1260
  R  E  N  I  T  S  I  M  K  M  G  P  L  S  K  L  S  G  M  I

TCCCGGTCTCTCCAACCTGACCGCGGGACTTGATGACGAAGACGGCTCCATGAAGCTCCG 1320
  P  G  L  S  N  L  T  A  G  L  D  D  E  D  G  S  M  K  L  R

CCGCATGATCTACATTTTCGACAGCATGACGGCCGCCGAACTCGACGGCGACGGCAAGAT 1380
  R  M  I  Y  I  F  D  S  M  T  A  A  E  L  D  G  D  G  K  M

GTTCGTCGAACAGCCTAGCCGCATGGTCCGGATCGCTTGCGGAAGCGGTACCACCGTCCG 1440
  F  V  E  Q  P  S  R  M  V  R  I  A  C  G  S  G  T  T  V  R

CGAAGTCGAAGACCTGCTCTCCCAGCACCGCATGATGGCTGGTATGGCCAAGCGCGTCGG 1500
  E  V  E  D  L  L  S  Q  H  R  M  M  A  G  M  A  K  R  V  G

CGGACAGAAGAAGCAGATGCAGCGTGCCCAGAACATGCTCAAGGGCGGTAACAAGGAACA 1560
  G  Q  K  K  Q  M  Q  R  A  Q  N  M  L  K  G  G  N  K  E  Q

GCAGCTCGCCGCCATGCAGAAGCGCATGGCCGCCATGGGTGGTGCTGGCGGTGGTGGATT 1620
  Q  L  A  A  M  Q  K  R  M  A  A  M  G  G  A  G  G  G  G  F

CCCCGGTATGCCCGGCATGGGCGACATGGCCAAGATGATGCAAATGCTGCAAGGTCAAGG 1680
  P  G  M  P  G  M  G  D  M  A  K  M  M  Q  M  L  Q  G  Q  G

AGGTGGCGGCGGTGGTGGTCTTCCCGGCCTGGGTGGGATGGACCTACAAAGTATGATGAG 1740
  G  G  G  G  G  L  P  G  L  G  G  M  D  L  Q  S  M  M  S

CCAGATGAGTGGATTGATGGGCGGTGGCGGTGGTGGTGGTGGCCGCGGTAGAGGACGGTG 1800
  Q  M  S  G  L  M  G  G  G  G  G  G  G  R  G  R  G  R

ATTGTGATGATGACGATGATGCACGCATTCTGAAATTCCTTCTTGACTTTTGATTTCGCG 1860

TTGTTACCATTCCATGATTATATTCTACACCTGTGCTCCGTCTCTTTTTTACGTTTGATT 1920

CTTAAGAGACTGGGATATATGGCCTTGCTTCAGTTCAGTCATCATTCACCTCATTCGTCG 1980
```

```
ATTGTAACTAGCATATGATGGCKKWTGGGCGTKACTTTGATTTTACTTGTKGYYTATCTT  2040
TTTTCTTYCTSGMTAATATCYGACTGGCCCTSTGGGGMATCAAATYTATGCTATSRAAGC  2100
TCAKYRSCCGCRAWYTTCGCCAGGTSMKATACTAAGTATWRRMCAWSKGRAAATATATCT  2160
ACAGAWYSTMGGKTGACKGKYAGSCTGCCAGWYACMWTGGAGCTWACTACTAAKAGCCST  2220
CGGACAGGTCATGACGAGTTTTCGTTGTTAATCGGGGCTTATTGGCTTGATTTGGCGCCG  2280
TGTGTTTGGCGCCTGTCTATCTACTTCCTTTCCGCTGCTGCCTTGGCCGCGCATTCTCGA  2340
GATCAAGATCGCTACAGGAAAGGCGCTGAGCACCACACGCCACGATGGGTTCCGCAACTA  2400
ACTTTGCCAAAACCATCATCATCCCCGCCGTGGATCTCCCTGAGCGCTTCWWAMTCCTGT  2460
TCTCCTTMSTGATCATNCCACCCGTAAGATGCTTTTCCTGTGACTGGTGAGTASTCAACC  2520
CAGTCATTCTGAGAATAGTGTATGCGGCGACCGAGTTGCTCTTGCCCGNCGTCAATACGG  2580
GATAATACCCGCGCCACATAGCAGAACTTTAAAAGTGCTCATCATTGGAAAACGTTCTTC  2640
GGGGCGRAAACTCTCAAGGATCTTACCGCTGTTGAGATCCAGTTCGATGTAACCCACTCG  2700
TGCACCCAACTGATCTTCAGCATCTTTTACTTTCACCAGCGTTTCTGGGTGASCAMAAAC  2760
AGGAAGSCAAAATSCCSCAMAAAAGGGAATAAGGGCGACACGGAAATGTTGAATACTCAT  2820
ACTCTTCCTTTTTCAATATTATTGAAGCATTTATCAGGGTTATTGTCTCATCCCGTAAAA  2880
CGACGGCCAGTGAGCGCGC  2899
```

FIG. 2c

```
GAATTCGCGGCCGCTAAGTGACGCATCTTTTAATTTGTACATGCTTTAATTTGGTTTATT  60

CCCTTTCTACAAGAATTCCCCCGCCATGGTCCTTCAGGATCTCGGGCGGCGAATCAACGC  120
                           M  V  L  Q  D  L  G  R  R  I  N  A

CGCCGTCAATGACCTGACTCGCTCCAACAATTTGGACGAGAAGGCCTTTGATGACATGAT  180
 A  V  N  D  L  T  R  S  N  N  L  D  E  K  A  F  D  D  M  I

TAAAGAGATCTGCGCCGCCCTGCTGTCCGCCGACGTCAACGTCCGCCTGGTCCAGTCCCT  240
 K  E  I  C  A  A  L  L  S  A  D  V  N  V  R  L  V  Q  S  L

CCGCAAGTCCATCAAATCCAGCGTCAACTTTGCCTCTCTTCCTGCCGCCGTGAACAAGAA  300
 R  K  S  I  K  S  S  V  N  F  A  S  L  P  A  A  V  N  K  K

GCGTTTGATTCAAAAGGCCGTCTTCGATGAGCTGGTTTCCCTGGTTGATCCCCATGCGGA  360
 R  L  I  Q  K  A  V  F  D  E  L  V  S  L  V  D  P  H  A  E

GCCCTTCCGCCCCAAGAAGGGCCGCTCCAACGTGATCATGTTCGTCGGTCTGCAGGGTGC  420
 P  F  R  P  K  K  G  R  S  N  V  I  M  F  V  G  L  Q  G  A

CGGTAAAACCACCACTTGTACCAAGCTGGCCCGCCACTACCAGATGCGCGGCTTCAAGAC  480
 G  K  T  T  T  C  T  K  L  A  R  H  Y  Q  M  R  G  F  K  T

TGCCCTCGTCTGTGCCGATACCTTCCGTGCTGGTGCTTTCGACCAGCTGAAGCAGAATGC  540
 A  L  V  C  A  D  T  F  R  A  G  A  F  D  Q  L  K  Q  N  A

CACCAAAGCCAAGATCCCCTACTACGGTAGCTTGACGCAAACCGACCCCGCCATTGTAGC  600
 T  K  A  K  I  P  Y  Y  G  S  L  T  Q  T  D  P  A  I  V  A

AGCCGAGGGTGTGGCCAAGTTCAAGAAGGAGCGTTTCGAAATCATCATCGTCGATACCAG  660
 A  E  G  V  A  K  F  K  K  E  R  F  E  I  I  I  V  D  T  S

TGGTCGTCACAAGCAGGAAGAAGAGCTTTTCACCGAAATGACCCAGATTCAGACCGCCGT  720
 G  R  H  K  Q  E  E  E  L  F  T  E  M  T  Q  I  Q  T  A  V

CACCCCCGACCAGACCATCCTCGTCCTCGACAGCACCATCGGTCAGGCTGCCGAAGCCCA  780
 T  P  D  Q  T  I  L  V  L  D  S  T  I  G  Q  A  A  E  A  Q

GTCCTCTGCCTTCAAGGCCACCGCAGACTTCGGAGCCATCATCATCACCAAGACGGATGG  840
 S  S  A  F  K  A  T  A  D  F  G  A  I  I  I  T  K  T  D  G

TCACGCCGCAGGTGGTGGTGCTATTTCCGCCGTCGCCGCCACACACTCCCATTATCTA  900
 H  A  A  G  G  G  A  I  S  A  V  A  A  T  H  T  P  I  I  Y

CCTCGGTACCGGTGAGCACCTGATGGATCTGGAACGCTTTGAGCCGAAGGCCTTCATCCA  960
 L  G  T  G  E  H  L  M  D  L  E  R  F  E  P  K  A  F  I  Q
```

```
GAAGCTCCTGGGTATGGGCGATATGGCTGGCCTGGTAGAGCACGTACAAGCCGTGACCAA  1020
 K  L  L  G  M  G  D  M  A  G  L  V  E  H  V  Q  A  V  T  K

GGACTCTGCCTCCGCCAAGGAAACCTACAAGCACATCTCCGAAGGTATCTACACGCTGCG  1080
 Q  S  A  S  A  K  E  T  Y  K  H  I  S  E  G  I  Y  T  L  R

TGACTTCCGCGAGAACATCACCTCCATCATGAAGATGGGACCCCTCTCCAAGCTCTCCGG  1140
 D  F  R  E  N  I  T  S  I  M  K  M  G  P  L  S  K  L  S  G

CATGATCCCCGGTCTATCCAACCTGACCGCGGGTCTCGATGACGAAGACGGCTCCATGAA  1200
 M  I  P  G  L  S  N  L  T  A  G  L  D  D  E  D  G  S  M  K

GCTCCGTCGCATGATCTACATTCTCGACAGTATGACGGCCGCCGAACTCGATGGCGATGG  1260
 L  R  R  M  I  Y  I  L  D  S  M  T  A  A  E  L  D  G  D  G

CAAGAATTTCGTCGAACAACCCAGCCGCATGGTCCGTATCGCCTGCGGAAGCGGTACCAC  1320
 K  N  F  V  E  Q  P  S  R  M  V  R  I  A  C  G  S  G  T  T

CGTCCGCGAAGTGGAAGACCTGCTCTCCCAGCACCGCATGATGGCCGGCATGGCCAAGCG  1380
 V  R  E  V  E  D  L  L  S  Q  H  R  M  M  A  G  M  A  K  R

TGTCGGTGGACAGAAGAAGCAGATGCAGCGCGCCCAGAACATGCTCAAGGGCGGTAACAA  1440
 V  G  G  Q  K  K  Q  M  Q  R  A  Q  N  M  L  K  G  G  N  K

GGAGCAGCAGCTCGCCGCCATGCAGAAGCGCATGGCCGCAATGGGTGGTGCCGGCGGTGG  1500
 E  Q  Q  L  A  A  M  Q  K  R  M  A  A  M  G  G  A  G  G  G

TGGATTCCCCGGTATGCCCGGCATGGGCGACATGGCCAAGATGATGCAAATGCTGCAAGG  1560
 G  F  P  G  M  P  G  M  G  D  M  A  K  M  M  Q  M  L  Q  G

TCAGGGAGGTGGAGGCGGCGGTGGTCTGCCCGGTCTAGGTGGAATGGATCTACAAAGTAT  1620
 Q  G  G  G  G  G  G  L  P  G  L  G  G  M  D  L  Q  S  M

GATGAGCCAGATGAGTGGGTTGATGGGCGGTGGCGGTGGTGGTGGTGGTGGAGGCCGCGG  1680
 M  S  Q  M  S  G  L  M (G  G  G  G  G  G  G  G  G) R  G

TAGAGGACGGTGATTGTGATGATGACGATGATGCACGCATTTCGAAACTCCTTTTTGATT  1740
 R  G  R

CATGTTTTCGCGTTGTTACCATTCCATGATTATATTACTACACCTGTGTCTCCGTCTCTT  1800

CTTTTCGTTTGATTTTTAAGAGACTGGGGATATATCGCCTTGCTTCAGTTCAGTCATCAT  1860

TCACCTCATTCGTCGATTGTAACTAGCATATGATGGTGTTGGGCGTGACTTTGATTTTAC  1920

TTRTTGCTTATCTTTTTTCTTTCTCGCTAATATCTGACTGGCCCTGTGGGGCATAAATTT  1980

ATGCTATGGAAGCACGGCCGCATTTCGCGGCCGCTAGAAGACCAACTGGTAACTCAGCGT  2040
```

CGGGTGACGGTCAGCCTGCCAGTCACATTGGACAACTCTAAGCGCCGTCACAGGTCATGA 2100

CGAGTTTTCGTTGTTAATCGGCTTATTGGCTTGATTTGGCGGTGTGTTTGGCGCCTGTCT 2160

ATCTA 2165

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 2877 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Aspergillus niger (ix) FEATURE:
      (A) NAME/KEY: CDS
      (B) LOCATION: join (126..203, 253..1776)

(xi) SEQUENCE DESCRIPTION: SEQ ID NO: 1:

```
ATCCTCCATT CGCTCTCTCC TGTCCTCTCT GCCACCTTTC ACGATTTCTG GCAGNAAGTG      60
```

```
ACGCATATTT TAATCTGTAC ATGCTTTAAT TTGATTTACC TCCTTTCGAC AAGAACTCCC        120

CCGCC ATG GTC CTT CAG GAT CTC GGG CGG CGA ATC AAC GCC GCC GTC AAT       170
      Met Val Leu Gln Asp Leu Gly Arg Arg Ile Asn Ala Ala Val Asn
        1           5                  10                  15

GAC CTG ACT CGC TCT AAC AAT TTG GAC GAG AAG GTGAGGATCA GCACTTTTCT       223
Asp Leu Thr Arg Ser Asn Asn Leu Asp Glu Lys
                20              25

CTCTGTCTGA TGTATGTACT GACTGTTAG CAG GCC TTT GAT GAC ATG ATC AAA         276
                                Gln Ala Phe Asp Asp Met Ile Lys
                                             30

GAG ATC TGC GCC GCC TTG CTG TCC GCC GAC GTC AAC GTC CGC CTG GTC         324
Glu Ile Cys Ala Ala Leu Leu Ser Ala Asp Val Asn Val Arg Leu Val
 35              40                  45                  50

CAG TCC CTC CGC AAA TCC ATC AAG TCC AGC GTC AAC TTT GCC TCT CTT         372
Gln Ser Leu Arg Lys Ser Ile Lys Ser Ser Val Asn Phe Ala Ser Leu
                55                  60                  65

CCT CCC GCC GTG AAC AAG AAG CGT TTG ATT CAG AAG GCC GTC TTC GAT         420
Pro Pro Ala Val Asn Lys Lys Arg Leu Ile Gln Lys Ala Val Phe Asp
                70                  75                  80

GAG CTG GTT TCC CTG GTT GAT CCC CAT GCG GAG CCA TTC CGT CCC AAG         468
Glu Leu Val Ser Leu Val Asp Pro His Ala Glu Pro Phe Arg Pro Lys
                85                  90                  95

AAG GGC CGC TCC AAC GTG ATC ATG TTC GTC GGT CTA CAG GGT GCC GGT         516
Lys Gly Arg Ser Asn Val Ile Met Phe Val Gly Leu Gln Gly Ala Gly
            100                 105                 110

AAA ACC ACC ACC TGT ACC AAG CTG GCC CGC CAC TAT CAG ATG CGC GGC         564
Lys Thr Thr Thr Cys Thr Lys Leu Ala Arg His Tyr Gln Met Arg Gly
115             120                 125                 130

TTC AAG ACC GCC CTC GTC TGT GCC GAT ACC TTC CGA GCT GGT GCT TTC         612
Phe Lys Thr Ala Leu Val Cys Ala Asp Thr Phe Arg Ala Gly Ala Phe
                135                 140                 145

GAC CAG CTG AAA CAG AAT GCC ACC AAG GCC AAG ATC CCC TAC TAC GGT         660
Asp Gln Leu Lys Gln Asn Ala Thr Lys Ala Lys Ile Pro Tyr Tyr Gly
            150                 155                 160

AGC CTG ACG CAA ACC GAC CCC GCC ATC GTG GCA GCC GAG GGT GTG GCC         708
Ser Leu Thr Gln Thr Asp Pro Ala Ile Val Ala Ala Glu Gly Val Ala
        165                 170                 175

AAG TTC AAG AAG GAG CGT TTC GAA ATC ATC ATT GTC GAT ACC AGT GGT         756
Lys Phe Lys Lys Glu Arg Phe Glu Ile Ile Ile Val Asp Thr Ser Gly
    180                 185                 190

CGT CAT AAG CAG GAA GAA GAG CTC TTC ACC GAA ATG ACC CAG ATT CAG         804
Arg His Lys Gln Glu Glu Glu Leu Phe Thr Glu Met Thr Gln Ile Gln
195                 200                 205                 210

ACC GCC GTC ACC CCC GAC CAG ACC ATC CTC GTC CTC GAC AGC ACC ATC         852
Thr Ala Val Thr Pro Asp Gln Thr Ile Leu Val Leu Asp Ser Thr Ile
                215                 220                 225

GGT CAG GCT GCC GAA GCC CAG TCC TCC GCC TTC AAG GCC ACC GCA GAC         900
Gly Gln Ala Ala Glu Ala Gln Ser Ser Ala Phe Lys Ala Thr Ala Asp
            230                 235                 240

TTC GGA GCC ATC ATC ATC ACC AAG ACG GAT GGT CAC GCC GCA GGT GGT         948
Phe Gly Ala Ile Ile Ile Thr Lys Thr Asp Gly His Ala Ala Gly Gly
        245                 250                 255

GGT GCT ATT TCC GCC GTC GCC GCC ACA CAC ACT CCC ATT ATC TAC CTC         996
Gly Ala Ile Ser Ala Val Ala Ala Thr His Thr Pro Ile Ile Tyr Leu
    260                 265                 270

GGT ACC GGT GAG CAC TTG ATG GAC CTG GAA CGT TTC GAG CCC AAG GCC        1044
Gly Thr Gly Glu His Leu Met Asp Leu Glu Arg Phe Glu Pro Lys Ala
275                 280                 285                 290

TTC ATC CAG AAG CTC CTG GGT ATG GGT GAT ATG GCC GGA CTG GTA GAG        1092
```

```
            Phe Ile Gln Lys Leu Leu Gly Met Gly Asp Met Ala Gly Leu Val Glu
                            295                 300                 305

CAC GTA CAA GCC GTG ACC AAG GAC TCG GCC TCC GCC AAG GAA ACA TAC            1140
His Val Gln Ala Val Thr Lys Asp Ser Ala Ser Ala Lys Glu Thr Tyr
            310                 315                 320

AAG CAC ATC TCA GAA GGT ATC TAC ACG CTG CGC GAC TTC CGC GAG AAC            1188
Lys His Ile Ser Glu Gly Ile Tyr Thr Leu Arg Asp Phe Arg Glu Asn
            325                 330                 335

ATC ACC TCC ATC ATG AAG ATG GGT CCT CTC TCC AAG CTC TCC GGC ATG            1236
Ile Thr Ser Ile Met Lys Met Gly Pro Leu Ser Lys Leu Ser Gly Met
            340                 345                 350

ATT CCC GGT CTC TCC AAC CTG ACC GCG GGA CTT GAT GAC GAA GAC GGC            1284
Ile Pro Gly Leu Ser Asn Leu Thr Ala Gly Leu Asp Asp Glu Asp Gly
355                 360                 365                 370

TCC ATG AAG CTC CGC CGC ATG ATC TAC ATT TTC GAC AGC ATG ACG GCC            1332
Ser Met Lys Leu Arg Arg Met Ile Tyr Ile Phe Asp Ser Met Thr Ala
            375                 380                 385

GCC GAA CTC GAC GGC GAC GGC AAG ATG TTC GTC GAA CAG CCT AGC CGC            1380
Ala Glu Leu Asp Gly Asp Gly Lys Met Phe Val Glu Gln Pro Ser Arg
            390                 395                 400

ATG GTC CGG ATC GCT TGC GGA AGC GGT ACC ACC GTC CGC GAA GTC GAA            1428
Met Val Arg Ile Ala Cys Gly Ser Gly Thr Thr Val Arg Glu Val Glu
            405                 410                 415

GAC CTG CTC TCC CAG CAC CGC ATG ATG GCT GGT ATG GCC AAG CGC GTC            1476
Asp Leu Leu Ser Gln His Arg Met Met Ala Gly Met Ala Lys Arg Val
            420                 425                 430

GGC GGA CAG AAG AAG CAG ATG CAG CGT GCC CAG AAC ATG CTC AAG GGC            1524
Gly Gly Gln Lys Lys Gln Met Gln Arg Ala Gln Asn Met Leu Lys Gly
435                 440                 445                 450

GGT AAC AAG GAA CAG CAG CTC GCC GCC ATG CAG AAG CGC ATG GCC GCC            1572
Gly Asn Lys Glu Gln Gln Leu Ala Ala Met Gln Lys Arg Met Ala Ala
            455                 460                 465

ATG GGT GGT GCT GGC GGT GGT GGA TTC CCC GGT ATG CCC GGC ATG GGC            1620
Met Gly Gly Ala Gly Gly Gly Gly Phe Pro Gly Met Pro Gly Met Gly
            470                 475                 480

GAC ATG GCC AAG ATG ATG CAA ATG CTG CAA GGT CAA GGA GGT GGC GGC            1668
Asp Met Ala Lys Met Met Gln Met Leu Gln Gly Gln Gly Gly Gly Gly
            485                 490                 495

GGT GGT GGT CTT CCC GGC CTG GGT GGG ATG GAC CTA CAA AGT ATG ATG            1716
Gly Gly Gly Leu Pro Gly Leu Gly Gly Met Asp Leu Gln Ser Met Met
500                 505                 510

AGC CAG ATG AGT GGA TTG ATG GGC GGT GGC GGT GGT GGT GGC CGC                1764
Ser Gln Met Ser Gly Leu Met Gly Gly Gly Gly Gly Gly Gly Arg
515                 520                 525                 530

GGT AGA GGA CGG TGATTGTGAT GATGACGATG ATGCACGCAT TCTGAAATTC                1816
Gly Arg Gly Arg

CTTCTTGACT TTTGATTTCG CGTTGTTACC ATTCCATGAT TATATTCTAC ACCTGTGCTC          1876

CGTCTCTTTT TTACGTTTGA TTCTTAAGAG ACTGGGATAT ATGGCCTTGC TTCAGTTCAG          1936

TCATCATTCA CCTCATTCGT CGATTGTAAC TAGCATATGA TGGCKKWTGG GCGTKACTTT          1996

GATTTTACTT GTKGYYTATC TTTTTTCTTY CTSGMTAATA TCYGACTGGC CCTSTGGGGM          2056

ATCAAATYTA TGCTATSRAA GCTCAKYRSC CGCRAWYTTC GCCAGGTSMK ATACTAAGTA          2116

TWRRMCAWSK GRAAATATAT CTACAGAWYS TMGGKTGACK GKYAGSCTGC CAGWYACMWT          2176

GGAGCTWACT ACTAAKAGCC STCGGACAGG TCATGACGAG TTTTCGTTGT TAATCGGGGC          2236

TTATTGGCTT GATTTGGCGC CGTGTGTTTG GCGCCTGTCT ATCTACTTCC TTTCCGCTGC          2296

TGCCTTGGCC GCGCATTCTC GAGATCAAGA TCGCTACAGG AAAGGCGCTG AGCACCACAC          2356
```

```
GCCACGATGG GTTCCGCAAC TAACTTTGCC AAAACCATCA TCATCCCCGC CGTGGATCTC    2416

CCTGAGCGCT TCWWAMTCCT GTTCTCCTTM STGATCATNC CACCCGTAAG ATGCTTTTCC    2476

TGTGACTGGT GAGTASTCAA CCCAGTCATT CTGAGAATAG TGTATGCGGC GACCGAGTTG    2536

CTCTTGCCCG NCGTCAATAC GGGATAATAC CCGCGCCACA TAGCAGAACT TTAAAAGTGC    2596

TCATCATTGG AAAACGTTCT TCGGGGCGRA AACTCTCAAG GATCTTACCG CTGTTGAGAT    2656

CCAGTTCGAT GTAACCCACT CGTGCACCCA ACTGATCTTC AGCATCTTTT ACTTTCACCA    2716

GCGTTTCTGG GTGASCAMAA ACAGGAAGSC AAAATSCCSC AMAAAAGGGA ATAAGGGCGA    2776

CACGGAAATG TTGAATACTC ATACTCTTCC TTTTTCAATA TTATTGAAGC ATTTATCAGG    2836

GTTATTGTCT CATCCCGTAA AACGACGGCC AGTGAGCGCG C                        2877
```

(2) INFORMATION FOR SEQ ID NO: 2:

(i) SEQUENCE CHARACTERISTICS:
        (A) LENGTH: 534 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Aspergillus niger (xi) SEQUENCE DESCRIPTION: SEQ ID NO: 2:

```
Met Val Leu Gln Asp Leu Gly Arg Arg Ile Asn Ala Ala Val Asn Asp
1               5                   10                  15

Leu Thr Arg Ser Asn Asn Leu Asp Glu Lys Gln Ala Phe Asp Asp Met
            20                  25                  30

Ile Lys Glu Ile Cys Ala Ala Leu Leu Ser Ala Asp Val Asn Val Arg
        35                  40                  45

Leu Val Gln Ser Leu Arg Lys Ser Ile Lys Ser Val Asn Phe Ala
    50                  55                  60

Ser Leu Pro Pro Ala Val Asn Lys Lys Arg Leu Ile Gln Lys Ala Val
65                  70                  75                  80

Phe Asp Glu Leu Val Ser Leu Val Asp Pro His Ala Glu Pro Phe Arg
                85                  90                  95

Pro Lys Lys Gly Arg Ser Asn Val Ile Met Phe Val Gly Leu Gln Gly
            100                 105                 110

Ala Gly Lys Thr Thr Thr Cys Thr Lys Leu Ala Arg His Tyr Gln Met
        115                 120                 125

Arg Gly Phe Lys Thr Ala Leu Val Cys Ala Asp Thr Phe Arg Ala Gly
    130                 135                 140

Ala Phe Asp Gln Leu Lys Gln Asn Ala Thr Lys Ala Lys Ile Pro Tyr
145                 150                 155                 160

Tyr Gly Ser Leu Thr Gln Thr Asp Pro Ala Ile Val Ala Ala Glu Gly
                165                 170                 175

Val Ala Lys Phe Lys Lys Glu Arg Phe Glu Ile Ile Val Asp Thr
            180                 185                 190

Ser Gly Arg His Lys Gln Glu Glu Glu Leu Phe Thr Glu Met Thr Gln
        195                 200                 205

Ile Gln Thr Ala Val Thr Pro Asp Gln Thr Ile Leu Val Leu Asp Ser
    210                 215                 220

Thr Ile Gly Gln Ala Ala Glu Ala Gln Ser Ser Ala Phe Lys Ala Thr
225                 230                 235                 240

Ala Asp Phe Gly Ala Ile Ile Ile Thr Lys Thr Asp Gly His Ala Ala
```

```
                        245                 250                 255
Gly Gly Gly Ala Ile Ser Ala Val Ala Ala Thr His Thr Pro Ile Ile
                260                 265                 270

Tyr Leu Gly Thr Gly Glu His Leu Met Asp Leu Glu Arg Phe Glu Pro
            275                 280                 285

Lys Ala Phe Ile Gln Lys Leu Leu Gly Met Gly Asp Met Ala Gly Leu
        290                 295                 300

Val Glu His Val Gln Ala Val Thr Lys Asp Ser Ala Ser Ala Lys Glu
305                 310                 315                 320

Thr Tyr Lys His Ile Ser Glu Gly Ile Tyr Thr Leu Arg Asp Phe Arg
                325                 330                 335

Glu Asn Ile Thr Ser Ile Met Lys Met Gly Pro Leu Ser Lys Leu Ser
            340                 345                 350

Gly Met Ile Pro Gly Leu Ser Asn Leu Thr Ala Gly Leu Asp Asp Glu
        355                 360                 365

Asp Gly Ser Met Lys Leu Arg Arg Met Ile Tyr Ile Phe Asp Ser Met
    370                 375                 380

Thr Ala Ala Glu Leu Asp Gly Asp Gly Lys Met Phe Val Glu Gln Pro
385                 390                 395                 400

Ser Arg Met Val Arg Ile Ala Cys Gly Ser Gly Thr Thr Val Arg Glu
                405                 410                 415

Val Glu Asp Leu Leu Ser Gln His Arg Met Met Ala Gly Met Ala Lys
            420                 425                 430

Arg Val Gly Gly Gln Lys Lys Gln Met Gln Arg Ala Gln Asn Met Leu
        435                 440                 445

Lys Gly Gly Asn Lys Glu Gln Gln Leu Ala Ala Met Gln Lys Arg Met
    450                 455                 460

Ala Ala Met Gly Gly Ala Gly Gly Gly Phe Pro Gly Met Pro Gly
465                 470                 475                 480

Met Gly Asp Met Ala Lys Met Met Gln Met Leu Gln Gly Gln Gly Gly
                485                 490                 495

Gly Gly Gly Gly Gly Leu Pro Gly Leu Gly Met Asp Leu Gln Ser
            500                 505                 510

Met Met Ser Gln Met Ser Gly Leu Met Gly Gly Gly Gly Gly
        515                 520                 525

Gly Arg Gly Arg Gly Arg
530

(2) INFORMATION FOR SEQ ID NO: 3:

(i) SEQUENCE CHARACTERISTICS:
        (A) LENGTH: 2166 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Aspergillus niger (xi) SEQUENCE DESCRIPTION: SEQ ID NO: 3:

GAATTCGCGG CCGCTAAGTG ACGCATCTTT TAATTTGTAC ATGCTTTAAT TTGGTTTATT      60

CCCTTTCTAC AAGAATTCCC CCGCC ATG GTC CTT CAG GAT CTC GGG CGG CGA     112
                              Met Val Leu Gln Asp Leu Gly Arg Arg
                                1               5

ATC AAC GCC GCC GTC AAT GAC CTG ACT CGC TCC AAC AAT TTG GAC GAG     160
Ile Asn Ala Ala Val Asn Asp Leu Thr Arg Ser Asn Asn Leu Asp Glu
```

-continued

```
       10                    15                    20                    25

AAG GCC TTT GAT GAC ATG ATT AAA GAG ATC TGC GCC GCC CTG CTG TCC           208
Lys Ala Phe Asp Asp Met Ile Lys Glu Ile Cys Ala Ala Leu Leu Ser
                30                    35                    40

GCC GAC GTC AAC GTC CGC CTG GTC CAG TCC CTC CGC AAG TCC ATC AAA           256
Ala Asp Val Asn Val Arg Leu Val Gln Ser Leu Arg Lys Ser Ile Lys
                    45                    50                    55

TCC AGC GTC AAC TTT GCC TCT CTT CCT GCC GCC GTG AAC AAG AAG CGT           304
Ser Ser Val Asn Phe Ala Ser Leu Pro Ala Ala Val Asn Lys Lys Arg
            60                    65                    70

TTG ATT CAA AAG GCC GTC TTC GAT GAG CTG GTT TCC CTG GTT GAT CCC           352
Leu Ile Gln Lys Ala Val Phe Asp Glu Leu Val Ser Leu Val Asp Pro
        75                    80                    85

CAT GCG GAG CCC TTC CGC CCC AAG AAG GGC CGC TCC AAC GTG ATC ATG           400
His Ala Glu Pro Phe Arg Pro Lys Lys Gly Arg Ser Asn Val Ile Met
 90                    95                   100                   105

TTC GTC GGT CTG CAG GGT GCC GGT AAA ACC ACC ACT TGT ACC AAG CTG           448
Phe Val Gly Leu Gln Gly Ala Gly Lys Thr Thr Thr Cys Thr Lys Leu
                       110                   115                   120

GCC CGC CAC TAC CAG ATG CGC GGC TTC AAG ACT GCC CTC GTC TGT GCC           496
Ala Arg His Tyr Gln Met Arg Gly Phe Lys Thr Ala Leu Val Cys Ala
                125                   130                   135

GAT ACC TTC CGT GCT GGT GCT TTC GAC CAG CTG AAG CAG AAT GCC ACC           544
Asp Thr Phe Arg Ala Gly Ala Phe Asp Gln Leu Lys Gln Asn Ala Thr
            140                   145                   150

AAA GCC AAG ATC CCC TAC TAC GGT AGC TTG ACG CAA ACC GAC CCC GCC           592
Lys Ala Lys Ile Pro Tyr Tyr Gly Ser Leu Thr Gln Thr Asp Pro Ala
        155                   160                   165

ATT GTA GCA GCC GAG GGT GTG GCC AAG TTC AAG AAG GAG CGT TTC GAA           640
Thr Lys Ala Lys Ile Pro Tyr Tyr Gly Ser Leu Thr Gln Thr Asp Pro
170                   175                   180                   185

ATC ATC ATC GTC GAT ACC AGT GGT CGT CAC AAG CAG GAA GAA GAG CTT           688
Ala Ile Val Ala Ala Glu Gly Val Ala Lys Phe Lys Lys Glu Arg Phe
                       190                   195                   200

TTC ACC GAA ATG ACC CAG ATT CAG ACC GCC GTC ACC CCC GAC CAG ACC           736
Glu Ile Ile Ile Val Asp Thr Ser Gly Arg His Lys Gln Glu Glu Glu
                   205                   210                   215

ATC CTC GTC CTC GAC AGC ACC ATC GGT CAG GCT GCC GAA GCC CAG TCC           784
Leu Phe Thr Glu Met Thr Gln Ile Gln Thr Ala Val Thr Pro Asp Gln
            220                   225                   230

TCT GCC TTC AAG GCC ACC GCA GAC TTC GGA GCC ATC ATC ATC ACC AAG           832
Thr Ile Leu Val Leu Asp Ser Thr Ile Gly Gln Ala Ala Glu Ala Gln
        235                   240                   245

ACG GAT GGT CAC GCC GCA GGT GGT GGT GCT ATT TCC GCC GTC GCC GCC           880
Ser Ser Ala Phe Lys Ala Thr Ala Asp Phe Gly Ala Ile Ile Ile Thr
250                   255                   260                   265

ACA CAC ACT CCC ATT ATC TAC CTC GGT ACC GGT GAG CAC CTG ATG GAT           928
Lys Thr Asp Gly His Ala Ala Gly Gly Gly Ala Ile Ser Ala Val Ala
                       270                   275                   280

CTG GAA CGC TTT GAG CCG AAG GCC TTC ATC CAG AAG CTC CTG GGT ATG           976
Ala Thr His Thr Pro Ile Ile Tyr Leu Gly Thr Gly Glu His Leu Met
                   285                   290                   295

GGC GAT ATG GCT GGC CTG GTA GAG CAC GTA CAA GCC GTG ACC AAG GAC          1024
Asp Leu Glu Arg Phe Glu Pro Lys Ala Phe Ile Gln Lys Leu Leu Gly
            300                   305                   310

TCT GCC TCC GCC AAG GAA ACC TAC AAG CAC ATC TCC GAA GGT ATC TAC          1072
Met Gly Asp Met Ala Gly Leu Val Glu His Val Gln Ala Val Thr Lys
        315                   320                   325

ACG CTG CGT GAC TTC CGC GAG AAC ATC ACC TCC ATC ATG AAG ATG GGA          1120
Asp Ser Ala Ser Ala Lys Glu Thr Tyr Lys His Ile Ser Glu Gly Ile
```

```
                330              335              340              345
CCC CTC TCC AAG CTC TCC GGC ATG ATC CCC GGT CTA TCC AAC CTG ACC         1168
Tyr Thr Leu Arg Asp Phe Arg Glu Asn Ile Thr Ser Ile Met Lys Met
                    350              355              360

GCG GGT CTC GAT GAC GAA GAC GGC TCC ATG AAG CTC CGT CGC ATG ATC         1216
Gly Pro Leu Ser Lys Leu Ser Gly Met Ile Pro Gly Leu Ser Asn Leu
                    365              370              375

TAC ATT CTC GAC AGT ATG ACG GCC GCC GAA CTC GAT GGC GAT GGC AAG         1264
Thr Ala Gly Leu Asp Asp Glu Asp Gly Ser Met Lys Leu Arg Arg Met
                    380              385              390

AAT TTC GTC GAA CAA CCC AGC CGC ATG GTC CGT ATC GCC TGC GGA AGC         1312
Ile Tyr Ile Leu Asp Ser Met Thr Ala Ala Glu Leu Asp Gly Asp Gly
                    395              400              405

GGT ACC ACC GTC CGC GAA GTG GAA GAC CTG CTC TCC CAG CAC CGC ATG         1360
Lys Asn Phe Val Glu Gln Pro Ser Arg Met Val Arg Ile Ala Cys Gly
410                 415              420              425

ATG GCC GGC ATG GCC AAG CGT GTC GGT GGA CAG AAG AAG CAG ATG CAG         1408
Ser Gly Thr Thr Val Arg Glu Val Glu Asp Leu Leu Ser Gln His Arg
                        430              435              440

CGC GCC CAG AAC ATG CTC AAG GGC GGT AAC AAG GAG CAG CAG CTC GCC         1456
Met Met Ala Gln Asn Met Leu Lys Arg Val Gly Gly Gln Lys Lys Gln Met
                    445              450              455

GCC ATG CAG AAG CGC ATG GCC GCA ATG GGT GGT GCC GGC GGT GGT GGA         1504
Gln Arg Ala Gln Asn Met Leu Lys Gly Gly Asn Lys Glu Gln Gln Leu
                    460              465              470

TTC CCC GGT ATG CCC GGC ATG GGC GAC ATG GCC AAG ATG ATG CAA ATG         1552
Ala Ala Met Gln Lys Arg Met Ala Ala Met Gly Gly Ala Gly Gly Gly
                    475              480              485

CTG CAA GGT CAG GGA GGT GGA GGC GGC GGT GGT CTG CCC GGT CTA GGT         1600
Gly Phe Pro Gly Met Pro Gly Met Gly Asp Met Ala Lys Met Met Gln
490                 495              500              505

GGA ATG GAT CTA CAA AGT ATG ATG AGC CAG ATG AGT GGG TTG ATG GGC         1648
Met Leu Gln Gly Gln Gly Gly Gly Gly Gly Leu Pro Gly Leu
                        510              515              520

GGT GGC GGT GGT GGT GGT GGT GGA GGC CGC GGT AGA GGA CGG TGA TTG         1696
Gly Gly Met Asp Leu Gln Ser Met Met Ser Gln Met Ser Gly Leu Met
                    525              530              535

TGA TGA TGA CGA TGA TGC ACG CAT TTC GAA ACT CCT TTT TGA TTC             1741
Gly Gly Gly Gly Gly Gly Gly Gly Gly Arg Gly Arg Gly Arg
                    540              545              550

ATGTTTTCGC GTTGTTACCA TTCCATGATT ATATTACTAC ACCTGTGTCT CCGTCTCTTC       1801

TTTTCGTTTG ATTTTTAAGA GACTGGGGAT ATATCGCCTT GCTTCAGTTC AGTCATCATT       1861

CACCTCATTC GTCGATTGTA ACTAGCATAT GATGGTGTTG GGCGTGACTT TGATTTTACT       1921

TRTTGCTTAT CTTTTTTCTT TCTCGCTAAT ATCTGACTGG CCCTGTGGGG CATAAATTTA       1981

TGCTATGGAA GCACGGCCGC ATTTCGCGGC CGCTAGAAGA CCAACTGGTA ACTCAGCGTC       2041

GGGTGACGGT CAGCCTGCCA GTCACATTGG ACAACTCTAA GCGCCGTCAC AGGTCATGAC       2101

CGAGTTTTCG TTGTTAATCG GCTTATTGGC TTGATTTGGC GGTGTGTTTG GCGCCTGTCT       2161

ATCTA                                                                   2166
```

(2) INFORMATION FOR SEQ ID NO: 4:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: Aspergillus niger (xi) SEQUENCE DESCRIPTION: SEQ ID NO: 4:

```
Met Val Leu Gln Asp Leu Gly Arg Arg Ile Asn Ala Ala Val Asn Asp
1               5                   10                  15

Leu Thr Arg Ser Asn Asn Leu Asp Glu Lys Ala Phe Asp Asp Met Ile
            20                  25                  30

Lys Glu Ile Cys Ala Ala Leu Leu Ser Ala Asp Val Asn Val Arg Leu
                35                  40                  45

Val Gln Ser Leu Arg Lys Ser Ile Lys Ser Ser Val Asn Phe Ala Ser
        50                  55                  60

Leu Pro Ala Ala Val Asn Lys Lys Arg Leu Ile Gln Lys Ala Val Phe
65                  70                  75                  80

Asp Glu Leu Val Ser Leu Val Asp Pro His Ala Glu Pro Phe Arg Pro
                85                  90                  95

Lys Lys Gly Arg Ser Asn Val Ile Met Phe Val Gly Leu Gln Gly Ala
                100                 105                 110

Gly Lys Thr Thr Thr Cys Thr Lys Leu Ala Arg His Tyr Gln Met Arg
            115                 120                 125

Gly Phe Lys Thr Ala Leu Val Cys Ala Asp Thr Phe Arg Ala Gly Ala
130                 135                 140

Phe Asp Gln Leu Lys Gln Asn Ala Thr Lys Ala Lys Ile Pro Tyr Tyr
145                 150                 155                 160

Gly Ser Leu Thr Gln Thr Asp Pro Ala Thr Lys Ala Lys Ile Pro Tyr
                165                 170                 175

Tyr Gly Ser Leu Thr Gln Thr Asp Pro Ala Ile Val Ala Ala Glu Gly
            180                 185                 190

Val Ala Lys Phe Lys Lys Glu Arg Phe Glu Ile Ile Val Asp Thr
            195                 200                 205

Ser Gly Arg His Lys Gln Glu Glu Leu Phe Thr Glu Met Thr Gln
    210                 215                 220

Ile Gln Thr Ala Val Thr Pro Asp Gln Thr Ile Leu Val Leu Asp Ser
225                 230                 235                 240

Thr Ile Gly Gln Ala Ala Glu Ala Gln Ser Ser Ala Phe Lys Ala Thr
                245                 250                 255

Ala Asp Phe Gly Ala Ile Ile Ile Thr Lys Thr Asp Gly His Ala Ala
                260                 265                 270

Gly Gly Gly Ala Ile Ser Ala Val Ala Ala Thr His Thr Pro Ile Ile
            275                 280                 285

Tyr Leu Gly Thr Gly Glu His Leu Met Asp Leu Glu Arg Phe Glu Pro
            290                 295                 300

Lys Ala Phe Ile Gln Lys Leu Leu Gly Met Gly Asp Met Ala Gly Leu
305                 310                 315                 320

Val Glu His Val Gln Ala Val Thr Lys Asp Ser Ala Ser Ala Lys Glu
                325                 330                 335

Thr Tyr Lys His Ile Ser Glu Gly Ile Tyr Thr Leu Arg Asp Phe Arg
            340                 345                 350

Glu Asn Ile Thr Ser Ile Met Lys Met Gly Pro Leu Ser Lys Leu Ser
            355                 360                 365

Gly Met Ile Pro Gly Leu Ser Asn Leu Thr Ala Gly Leu Asp Asp Glu
    370                 375                 380

Asp Gly Ser Met Lys Leu Arg Arg Met Ile Tyr Ile Leu Asp Ser Met
385                 390                 395                 400
```

```
Thr Ala Ala Glu Leu Asp Gly Asp Gly Lys Asn Phe Val Glu Gln Pro
            405                 410                 415

Ser Arg Met Val Arg Ile Ala Cys Gly Ser Gly Thr Thr Val Arg Glu
            420                 425                 430

Val Glu Asp Leu Leu Ser Gln His Arg Met Met Ala Gly Met Ala Lys
            435                 440                 445

Arg Val Gly Gly Gln Lys Lys Gln Met Gln Arg Ala Gln Asn Met Leu
            450                 455                 460

Lys Gly Gly Asn Lys Glu Gln Gln Leu Ala Ala Met Gln Lys Arg Met
465                 470                 475                 480

Ala Ala Met Gly Gly Ala Gly Gly Gly Phe Pro Gly Met Pro Gly
                485                 490                 495

Met Gly Asp Met Ala Lys Met Met Gln Met Leu Gln Gly Gln Gly Gly
            500                 505                 510

Gly Gly Gly Gly Gly Leu Pro Gly Leu Gly Gly Met Asp Leu Gln Ser
            515                 520                 525

Met Met Ser Gln Met Ser Gly Leu Met Gly Gly Gly Gly Gly Gly
            530                 535                 540

Gly Gly Gly Arg Gly Arg Gly Arg
545                 550
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (D) OTHER INFORMATION: N is inosine (xi) SEQUENCE DESCRIPTION: SEQ ID NO:5:

CARGGNNNWG GKAARACNAC                                      20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (D) OTHER INFORMATION: N is inosine (xi) SEQUENCE DESCRIPTION: SEQ ID NO:6:

TTYGAYCARY TNAARCARAA                                      20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (D) OTHER INFORMATION: N is inosine

```
           (xi) SEQUENCE DESCRIPTION: SEQ ID NO:7:

TTYTGYTTNA RYTGRTCRAA                                               20

(2) INFORMATION FOR SEQ ID NO:8:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (ix) FEATURE:
           (D) OTHER INFORMATION: N is inosine (xi) SEQUENCE DESCRIPTION: SEQ ID NO:8:

TTYTCNCCNG TNCCDARTAA                                               20

(2) INFORMATION FOR SEQ ID NO:9:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:9:

TAGGATCCCC AATGGTCCTT CAGGATCTCG G                                  31

(2) INFORMATION FOR SEQ ID NO:10:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:10:

TTGGCTTTGG TGGCATTCTG                                               20
```

GENES ENCODING SIGNAL RECOGNITION PARTICLE OF ASPERGILLUS NIGER

FIELD OF THE INVENTION

The present invention relates to the genes encoding proteins involved in protein translocation within eukaryotic cells. More specifically, the invention relates to genes encoding components of a filamentous fungal signal recognition particle.

BACKGROUND OF THE INVENTION

The pathway followed by secreted proteins within the cell has been studied in prokaryotes, yeast and mammalian cells. A secreted protein must first be targeted to its destination, and then must be able to cross the target organelle membrane. In recent years a great deal has been learned about the process of targeting or translocation of proteins from the cytoplasm into the endoplasmic reticulum (ER). A secretory signal peptide in the primary amino acid sequence targets the protein for secretion. The translocation process of secretory proteins into the ER, begins on the ribosomes in the cytoplasm. Once the signal peptide is synthesized and emerges from the ribosome, a cytosolic factor, the signal recognition particle, or SRP, binds to the signal peptide and to the ribosome, causing translational arrest. The nascent peptide/SRP/ribosome complex is recognized by an SRP receptor (SRP docking protein) in the ER membrane and binds to it; the signal peptide is then displaced from the SRP, in steps requiring GTP hydrolysis. Protein synthesis then continues, and the nascent protein enters the ER (Walter and Lingappa, Ann. Rev. Cell Biol. 2: 499–516, 1986; Simon, Current Opinion in Cell Biology 5: 581–588, 1993).

The SRP is a ribonucleoprotein composed of a single RNA molecule (7S RNA) and 6 polypeptides identified by their molecular weights: 9 kDa, 14 kDa, 19 kDa, 54 kDa, 68 kDa, and 72 kDa (Walter and Blobel, Nature 299: 691–698, 1982; Siegel and Walter, J. Cell Biol. 100: 1913–1921, 1989). Genes coding for the 54 kDa subunit of SRP have been cloned from higher eukaryotes (murine and canine; Bernstein et al., Nature 340: 482–486, 1989; Romisch et al. Nature 340: 478–482, 1989, respectively), *Saccharomyces cerevisiae* and *Schizosaccharomyces pombe* (Hann et al. J. Cell Biol. 109: 3223–3230); and *Arabidopsis thaliana* (Lindstrom et al., Plant Molecular Biology 23: 1265–1272, 1993). Analysis of these genes has revealed that the protein consists of two functional domains. Using fine resolution cross linking for nascent secretory peptide chains to SRP, it has been demonstrated that the C-terminal half of the protein binds to the signal peptide (Kurzhchalia et al., Nature 320: 634–636, 1986; Krieg et al., Proc. Nat. Acad. Sci. 83: 8604–8606, 1986). This domain is referred to as the M-domain due to its high percentage of methionine residues. The N-terminal half of the protein has been identified as a GTP binding domain, based on amino acid homologies with consensus GTP binding motifs (Bernstein et al., Nature 340: 482–486, 1989; Romisch et al. Nature 340: 478–482, 1989).

There have been no previous studies on the SRPs of filamentous fungi. Filamentous fungi are now commonly used as host cells for expression of recombinant protein, and there is an ongoing search for means to enhance levels of secretion of a protein of interest. Isolation of the genes encoding crucial units of the secretory pathway will facilitate this process. To that end, the present invention provides a gene encoding an SRP subunit, and thus also provides a means of increasing heterologous protein secretion in filamentous fungal host cells.

SUMMARY OF THE INVENTION

The present invention relates to a nucleic acid construct containing a nucleic acid sequence encoding an element of a filamentous fungal signal recognition peptide (SRP). In a preferred embodiment, the element is an SRP subunit, most preferably SRP54. As used herein, "nucleic acid construct" is intended to indicate any nucleic acid molecule of cDNA, genomic DNA, synthetic DNA or RNA origin. The term "construct" is intended to indicate a nucleic acid segment which may be single-or double-stranded, and which may be isolated in complete or partial form from a naturally occurring gene or which has been modified to contain nucleic acid segments which are combined and juxtaposed in a manner which would not otherwise exist in nature. The construct may optionally contain other nucleic acid segments. In a preferred embodiment, the construct contains a nucleic acid sequence encoding an Aspergillus SRP54 subunit.

The constructs of the invention are useful in creating novel vectors which are useful in increasing the expression of the subunit. Such vectors can then be used, in combination with a gene encoding a protein of interest, to transform host cells, preferably filamentous fungal host cells, for expression of the protein of interest. The combination of the increased production of the secretory component in the host cell containing the gene encoding the protein of interest can enhance the yield of the protein of interest by the host cell. Thus, the invention also provides a method for recombinant production of a protein, wherein a filamentous fungal host strain which produces larger amounts of one or more of the components of the eukaryotic secretory pathway than a wild-type strain cultured under the same conditions, is cultured under conditions which are conducive to the expression of the secretory component and the protein of interest. In a preferred embodiment, the component is SRP54.

BRIEF DESCRIPTION OF THE DRAWINGS

FIG. 1 shows an alignment of predicted proteins coded for by two SRP54 PCR products (SEQ ID NOS: 2 and 4).

FIG. 2 shows the nucleotide and predicted amino acid sequence of *Aspergillus niger* Bo1 genomic clone (SEQ ID NOS 1 and 2).

FIG. 3 shows the nucleotide and predicted amino acid sequence of *Aspergillus niger* SFAG2 cDNA clone (SEQ ID NOS: 3 and 4).

DETAILED DESCRIPTION OF THE INVENTION

In an attempt to isolate an Aspergillus SRP54 gene, four degenerate oligonucleotide primers complementary to conserved regions among previously cloned SRP54 genes are designed, and used in PCR reactions with *A. oryzae* genomic DNA. Reactions with a combination of two of these primers yields a number of reaction products. A significant amplification product of the successful primers is approximately 500 bp, which is the size predicted for SRP54. This fragment is purified and used as a template for further PCR experiments with a different pair of primers to determine if the fragment is specific for SRP54 based on published yeast amino acid sequence. A 390 bp product, corresponding to the predicted size, is obtained. The 500 bp product is then subcloned and five subclones sequenced. Two subclones, based on homology to previously isolated SRP54 genes, appear to code for the Aspergillus SRP54 gene. However, the sequences are not identical, suggesting the possibility of two SRP54 genes (FIG. 1). Southern hybridization of the 500 bp product with genomic DNA of two different Aspergillus species reveals a single band in each digest, indicating a either a single gene, or two tightly linked genes.

To clone the genomic sequences, an Bo-1 *A. niger* lambda EMBL library is screened with the 500 bp PCR product. DNA from four purified positives is subjected to restriction enzyme mapping; four contain BamHI, HindIII, and SalI fragments of the same size. The 7.5 kb HindIII fragment is subcloned and characterized. The hybridization of the SRP54 probe is found to be restricted to a 4.5 kb ClaI fragment. The open reading frame on this fragment is found to have a sequence encoding a 26 amino acid N-terminus which is 67% identical to the SRP54 N-terminus of *S. cerevisiae*. The complete sequence of the genomic clone is shown in FIG. 2.

Isolation of a cDNA clone is also undertaken. A full length copy of the SRP54 cDNA is identified from an *A. niger* SFAG2 cDNA library. The sequence of the cDNA clone is presented in FIG. 3; at the DNA level, there are a number of base changes in the wobble position relative to the *A. niger* Bo1 SRP54 gene, giving a 98% homology between the sequences from the two strains. An insertion near the C-terminus gives two additional glycine residues in SFAG2.

The *Aspergillus niger* SRP54 protein is encoded by two exons of 78 and 1587 bp, with a 49 bp intron. There is an overall 53% amino acid identity with the SRP54 gene of *S. cerevisiae;* however, in the GTP binding region, the homology is 63%, and in the M-domain, there is only 43% identity.

The present invention is not limited to the use of the sequences disclosed in FIGS. 2 and 3, or the coding regions depicted therein. The difference in sequence shown for two strains of the same species shows that variation within the sequence of a single species is tolerated, and using the techniques described herein, such variants can readily be identified. Therefore, when "*A. niger*" is referred to in this context, it will be understood to encompass all such variations. In addition, the isolated gene provides a means for isolating homologous genes from other filamentous fungi, such as other Aspergillus species, e.g., *A. oryzae, A. foetidus, A. japonicus, A. aculeatus,* or *A. nidulans*. Other non-Aspergillus filamentous species include Fusarium species, such as *F. graminearum, F. oxysporum, F. solani, F. culmorum* (or corresponding teleomorphs), *Neurospora crassa, Trichoderma reesei, T. viridae, T. harzianum, T. longibranchiatum, Penicillium janthinellum, P. notatum, P. chrysogenum, P. camemberti, P. roqueforti, Humicola insolen, H. grisea* var. *thermoidea, H. lanuginosa, Scytalidium thermophilum, Myceliophthora thermophila,* and *Thielavia terrestris*. The gene, the 500 bp fragment described above, or an oligonucleotide based thereon, can be used as probes in southern hybridization to isolate homologous genes of these other species. In particular, such probes can be used under low to high stringency conditions (for example, prehybridization and hybridization at 42° C. in 5× SSPE, 0.3% SDS, 200 μg/ml sheared and denatured salmon sperm DNA, and either 50, 35 or 25% formamide for high, medium and low stringencies, respectively) for hybridization with the genomic or cDNA of the species of interest, following standard southern blotting procedures, in order to identify and isolate the corresponding SRP54 gene therein. A PCR reaction using the degenerate probes mentioned herein and genomic DNA or first-strand cDNA from a filamentous fungus may also yield a SRP54-specific product which could then be used as a probe to clone the corresponding genomic or cDNA. In a preferred embodiment the homologous genes encode a protein having at least about 60% homology, more preferably at least 70% homology, and most preferably at least 80% homology, with the amino acid sequence depicted in FIGS. 2 and 3.

The gene of the present invention is useful in enhancing recombinant expression of a protein of interest in a host cell, by optimizing the secretory pathway of a eukaryotic host cell. In a particular embodiment, the amount of SRP is increased by creating a host cell containing one or more additional copies of the SRP gene or subunits thereof, as well as the gene encoding the protein of interest, and culturing the host cell under conditions conducive to expression of the genes, so that the yield of the protein of interest is increased relative to a host cell in which the SRP copy number has not been increased. This can be achieved with an SRP homologous or heterologous to the host cell. Increasing copy number can be achieved by transforming a strain with the expression construct one or more times. Alternately, it can be increased by whole cell mutagenesis. Increase in the amount of SRP54 protein can also be achieved by placing the SRP54 gene under the control of a strong promoter, either constitutive or regulated. One example of such a promoter is the glucoamylase promoter.

Such a strategy can also be applied to enhance yield by increasing expression of other components of the secretory machinery. For example, such enhancement may be achieved using any one, or combination of all of the subunits of the filamentous fungal signal recognition particle. Isolation and identification of other fungal subunits can be achieved by production of a polyclonal or monoclonal antibody against the SRP54 subunit protein, which antibody in turn can be used to precipitate the signal recognition particle complex from cellular material. Such material provides the basis for characterization and cloning of other subunits in the complex. In addition to the signal recognition particle, overexpression of components such as protein conducting channels of the ER membrane (BioEssays 14: 535–540), the ER docking protein or receptor, the BiP protein (Nature 355: 35–45), the Sec series of genes (e.g., Sec-14, Sec-59, Sec-61, Sec-62, and Sec-63) and signal peptidase. Moreover, mutated sequences of the foregoing proteins can also be used in protein overexpression, in that such mutants may have enhanced activity relative to the wild-type protein (Perez-Perez, et al. Bio/Technology 12:178–180, 1994).

Host cells containing the constructs of the present invention are particularly useful in the expression of heterologous protein. Preferred host cells are filamentous fungi, such as those species identified above. In a preferred embodiment, the host cell is a member of the genus Aspergillus. However, any eukaryotic host cell employing a similar secretory mechanism can be used for this purpose. Other useful host cells include yeast cells, insect cells, and mammalian cells. By "heterologous protein" in the present context is meant a protein which is not native to the host cell, a native protein in which modifications have been made to alter the native sequence, or a native protein whose expression is quantitatively altered as a result of a manipulation of the host cell by recombinant DNA techniques. Also encompassed within this term are native proteins for which expression in the host cells involves the use of genetic elements not native to the host cell, or use of native elements which have been manipulated to function in a manner not normally seen in the host cell.

The host cells of the present invention can be used in recombinant protein production using art-recognized methodology. The SRP54 gene, SRP subunit, or other secretory component can be expressed, in active form, using an expression vector, as will be the protein of interest. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the protein of interest, nucleotides encoding a signal sequence may be inserted prior to the coding sequence of the gene. For expression under the direction of control sequences, a gene to be used according to the invention is operably linked to the control sequences in the proper reading frame.

The expression vector may be any vector which may conveniently be subjected to recombinant DNA procedures, and the choice of vector will typically depend on the host cell into which it is to be introduced. In a preferred embodiment of the present invention, the host cell is a strain of the genus Aspergillus. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the gene encoding the protein of interest should be operably connected to a suitable promoter sequence. The promoter may be any DNA sequence which shows transcriptional activity in the host cell of choice and may be derived from genes encoding proteins either homologous or heterologous to the host cell. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the protein of interest. Termination and polyadenylation sequences may suitably be derived from the same sources as the promoter. The vector may further comprise a DNA sequence enabling the vector to replicate in the host cell in question.

The vector may also comprise a selectable marker, e.g. a gene the product of which complements a defect in the host cell, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of *A. nidulans* or *A. oryzae*. Furthermore, selection may be accomplished by co-transformation, e.g. as described in WO 91/17243.

It is generally preferred that the expression of the protein of interest gives rise to a product which is extracellular. The protein of interest may thus comprise a preregion permitting secretion of the expressed protein into the culture medium. If desirable, this preregion may be native to the protein of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The host cells comprising enhanced secretory components can be used to express any prokaryotic or eukaryotic protein of interest, and are preferably used to express eukaryotic proteins. Of particular interest for these cells is their use in expression of fungal enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The host cells can also be used to express heterologous proteins of pharmaceutical interest such as hormones, growth factors, receptors, and the like.

The invention will be further illustrated by the following non-limiting examples.

EXAMPLES

I. Materials and Methods

Strains—The following strains are used in the experiments described below:*Escherichia coli* K802 (el4-(mrcA), mrcB, hsdR2, galK2, GalT22, supE44, metB1), *E. coli* SOLR (el4-(mcrA), D(mcrCB-hsdSMR-mr$^r$)171, sbcC, recB, recJ, uvrC, umuC::Tn5(kan$^r$), lac, gyrA96, relA1, thi-1, endA1, 1$^R$[F'proAB1acI$^q$ZDM15]Su$^-$, *E. coli* JM101supE, thi-1, A(lac-proAB),[F'traD36, proAB, lacI$^Q$ZDM15], *E. coli* XL-1 Blue recA1, endA1, gyrA96, thi-1, hsdR17, supE44, relA1, lac,[F'proAB, lac$^q$ZDM15, Tn10(tet$^r$)], *A. niger* ATCC1040, *A. niger* Bo1, *A. niger* SFAG, *A. oryzae* HowB104.

PRC amplification of SRP54—The amplification of an SRP54 gene fragment from *Aspergillus oryzae* genomic DNA is performed under the following conditions: 0.4 units of Taq polymerase, 1$\mu$ mole DNA primers, 100 ng DNA template, 200 $\mu$mole each of dATP, dCTP, dGTP, TTP, in 1× buffer (Boehringer Mannheim, Indianapolis, Ind.). The following are used in reactions for 1 cycle of 94° C./5 minutes followed by 30 cycles of 94° C./1 minute, 50° C./1 minute, 72° C./1 minute in an Ericomp PCR machine.

Primer A(93-840): CARGGNWSSGGKAARACNAC (SEQ ID NO: 5)
Primer B(93-843): TTYGAYCARYTSAARCARAA (SEQ ID NO: 6)
Primer C(93-842): TTYTGYTTSARYTGRTCRAA (SEQ ID NO: 7)
Primer D(93-837): TTYTCSCCNGTSCCDARTAA (SEQ ID NO: 8)

In the above primers S represents inosine, Y represents deoxyribonucleotides C or T, R represents nucleotides A or G, D represents nucleotides A,G, or T, and N represents deoxyribonucleotides G, A, T or C.

Subcloning of PCR products—PCR products are subclones for sequencing using the TA cloning kit (Invitrogen, San Diego, Calif.) following the manufacturers' protocols.

Lambda libraries—A cDNA library of A. niger SFAG2 mRNA is prepared using a Pharmacia cDNA kit. The library contains abut 700,000 recombinant phage of a total of 830,000 (84% recombinant). Bluescript plasmids are rescued from the SRP54 Lambda Zap clones according to protocols provided by Stratagene (LaJolla, Calif.).

An A. niger Bo1 genomic library is prepared by partially digesting Bo1 genomic DNA with Sau3A and isolating DNA fragments greater than 10 kb. These DNA fragments are ligated into BamHI digested lambda EMBL4 arms (Clontech, Palo Alto, Calif.). The library is amplified according to standard protocols.

DNA Sequencing—Nucleotide sequences are determined using Taq polymerase cycle-sequencing with fluorescent labeled dideoxynucleotides. The sequencing reactions are electrophoresed on an Applied Biosystems automatic DNA sequencer (Model 373A, version 1.2.0). In addition to SRP54 specific primers, the M13 reverse(-48) and M13 (-20) forward primers are used (Sanger et al., J. Mol. Biol. 143: 163–178).

II. Results and Discussion

Four pools of degenerate oligonucleotides based on the three conserved regions found in known SRP54 genes are used in PCR experiments with A. oryzae HowB104 genomic DNA as the template. Reactions with a combination of primers A and D produced several reaction products. Combinations of the other primers fails to produce any product. A major amplification product in experiments with primers A and D, is approximately 500 bp, the predicted size according to known SRP54 sequences. The 500 bp amplified fragment is purified and used as a template in a second round of PCR reactions using primers C and D in order to confirm it is specific for the SRP54 gene. A single 390 bp product is synthesized in this reaction corresponding to the predicted size. The 500 product synthesized with primers A and D is subcloned using the TA cloning Kit. Five subclones are subjected to DNA sequencing using M13 reverse and M13 primers. Based on homology to previously cloned SRP54 genes, two of the clones appeared to code for SRP54 (71% identity to the SRP54 of S. cerevisiae). However, the sequences of these two subclones are not identical, raising the possibility of two SRP54 genes.

To determine the number of SRP54 genes in Aspergillus, a Southern blot of genomic DNA from A. niger ATCC1040 and A. oryzae HowB104 is probed with the 500 bp PCR product pool. Hybridization conditions are 5× SSPE, 0.3% SDS, 200 μg/ml sheared salmon sperm DNA and 50%, 35%, or 25% formamide at 42° C., washed at 42° C. for 15 minutes, in 2× SSC; 15 minutes in 1× SSC, 0.1% SDS and 15 minutes in 0.5× SSC, 0.1% SDS. Only one band in each digest hybridizes with the SRP54 probe; thus, it is concluded that A. oryzae and A. niger contain a single copy of the SRP54 gene. However, the possibility of two tightly linked genes cannot be ruled out. Another explanation for the sequence differences is the introduction of nucleotide errors by Taq DNA polymerase during PCR amplification.

In order to clone the genomic sequences for SRP54, an A. niger Bo1 lambda EMBL4 library (26,500 recombinants) is screened using the 500 bp SRP54 PCR product pool as a probe. More than 30,000 plaques are probed, and 6 positives isolated. After purification, 5 of the original positive clones continued to hybridize with the SRP54 probe. These are analyzed further by Southern blot four of these clones contain the same size BamHI, HindIII, and SalI fragments which hybridize to the probe. A 7.5 kb HindIII fragment common to all clones is subcloned(pDSY16) and further characterized. Hybridization of the SRP54 probe to pDSY16 is localized to a 4.5 kb ClaI fragment. DNA sequencing of this fragment reveals an open reading frame beginning 150 bp in from one of the ClaI sites. This proposed open reading frame encodes a 26 amino acid peptide having 67% identity to the N-terminus of the S. cerevisiae SRP54 protein, thus identifying it as the A. niger SRP54 homologue. The complete DNA sequence of the Bo1 SRP54 gene is determined for the coding and noncoding strands, and is shown in FIG. 2. The protein is encoded by two exons, 78 and 1587 bp respectively, separated by a 49 bp intron. The protein shares 53% amino acid identity to the SRP54 protein from S. cerevisiae. When only the GTP binding domain (amino acids 1–277) is compared to the corresponding domain of S. cerevisiae, homology increases to 63%. In contrast, the methionine rich M-domain (amino acids 278–533) is only 43% identical to that of S. cerevisiae. The methionine content for both M-domains however, is conserved at 11% (29 residues in S. cerevisiae and 30 residues in A. niger).

An A. niger SFAG2 cDNA library in Lambda Zap II is probed with the A. oryzae 500 bp PCR fragment pool in an attempt to isolate an A. niger cDNA clone encoding SRP54 using hybridization conditions listed above. More than 42,000 plaques are screened and 5 positives are identified. After purification, 4 clones continue to hybridize with the probe. Plasmid DNA is isolated from 2 of these clones and characterized by DNA sequencing (the fourth clone is not analyzed further). The first, designated pShTh24, encodes a full length copy of Aspergillus SRP54. The second clone, ShTh6.2, encodes an incomplete cDNA beginning at amino acid residue 230 of SRP54. The complete DNA sequence of the SRP54 open reading frame of pShTh24 is determined for both coding and noncoding strands, and is shown in FIG. 3. At the DNA level, SFAG2 SRP54 contains several base changes in the wobble position making the DNA sequence 98% homologous compared to that of Bo1 SRP54(FIG. 1). An insertion of 6 bp near the C-terminus of the SFAG2 SRP54 coding sequence introduces an additional two glycine residues.

An SRP54 expression construct is made by placing the gene under the control of the TAKA promoter and AMG terminator using vector pTOC68. First, a BamHI restriction site is placed immediately upstream of the SFAG2 coding sequence by adding a BamHI site at the end of the following PCR primer(94–648): TAGGATCCCCAATGGTCCT-TCAGGATCTCGG (SEQ ID NO: 9). This primer is used in conjunction with a second primer(94-678), that is homologous to bases 448 to 467 downstream of the ATG start codon: TTGGCTTTGGTGGCATTCTG (SEQ ID NO: 10).

PCR reactions are run under the following conditions: 100 ng pShTh24 (a cDNA clone in a Bluescript vector), 1 μmole DNA primers, 200 mmole each of dATP, dCTP, dGTP, TTP, 0.4μ Taq DNA polymerase, in 1× Taq buffer (Boehringer Mannheim, Indianapolis, Ind.) are mixed together and amplified 30 cycles 94° C./1 minute, 58° C./1 minute, 72° C./1 minute. The PCR product is purified and digested with BamHI, AatI and then ligated with pTOC68 digested with BamHI, XhoI and pShTh24 AatI, XhoI purified 2 kb fragment under standard conditions. The resulting plasmid, ShTh29, is digested with XhoI to completion followed by a partial digest with SfuI. The 6.2 kb fragment is gel isolated from the other fragments and treated with T4 DNA polymerase klenow fragment. The reaction is then self-ligated and transformed into DH5α competent cells. The resulting plasmid is named pShTh29Δ.

The expression plasmid is used in transformation of Aspergillus strains previously transformed with pDSY10 for the increased expression of laccase. The laccase plasmid, pDSY10, contains a full-length laccase cDNA gene, including signal sequence, from *Polyporus pinsitus,* with a TAKA promoter and AMG terminator. An additional plasmid containing a selectable marker, either amdS or pyrG, is also added to the transformation.

For transformation, 500 ml YEG+1M sucrose medium is inoculated with 100 μl of conidial suspension of the strain to be transformed and incubated overnight at 37° C. The medium is removed from the mat, and 500 μl OM(1.2M MgSO$_4$, 10 mM NaPO$_4$ buffer, pH 5.8) plus Novozyme® 5 mg/ml and BSA 1 mg/ml) is added. The fungal mat is broken up by pipetting the mixture up and down several times. The plate is placed in a 34° C. shaker set at 90 rpm. Protoplasting is completed in about an hour. The protoplast mixture is placed in an eppendorf tube, and 1 ml STC added and mixed. The mixture is spun in a centrifuge for 8 minutes at 6000 rpm. The supernatant is poured off and 1 ml STC (0.8M sorbitol, 50 mM Tris pH8, 50 mM CaCl$_2$) is added and mixed. The mixture is spun at 3000 rpm for 5 minutes, then the procedure repeated, The protoplasts are collected and resuspended in STC at a concentration of $2-5\times10^7$ protoplasts/ml.

100 μl of protoplast suspension is mixed with 5–10 μg of the appropriate DNA in 10 μl of STC. One ml PTC (40% PEG 4000, 50 mM Tris pH 8, 50 mM CaCl$_2$) is added and mixed thoroughly. The mixture is incubated at room temperature for 20 minutes. Protoplasts are then plated onto agar plates containing the appropriate media for the selectable marker used in the transformation.

Transformants are initially screened for increased production of laccase. This is done by plating transformants on ABTS agar plates (1% glucose, 1 μm ABTS, in Aspergillus minimal medium), and looking for increased green halo size over that of the untransformed parent strain. Those transformants with larger halos are then assayed for production of laccase by ABTS assay (One ml broth samples are assayed with 1 mM ABTS in 100 mM acetate buffer pH 5.0 for 1 minute. Assay results are recorded as the change in absorbance at 418 nm per minute per ml). DNA from the top four producers of laccase is isolated, digested with EcoRI and subjected to Southern analysis by probing with both SRP54 and OliC coding sequences. Quantification of the signal produced by hybridization of the SRP54 probe to SRP54 in comparison with the signal produced by the OliC probe hybridizing to OliC (a single copy gene in Aspergillus), reveals the gene copy number of SRP54 in each of the transformants.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604 and given the following accession numbers.

| Cell line | Accession No. |
|---|---|
| *E. coli* containing pShTh24 (EMCC #0121) | NRRL B-21327 |

What is claimed is:

1. A nucleic acid construct comprising a nucleic acid sequence encoding an SRP54 protein which is:
   (a) a nucleic acid sequence which encodes an SRP54 protein having the amino acid sequence of SEQ ID NO:2 or SEQ ID NO:4; or
   (b) a nucleic acid sequence obtained from an Aspergillus strain which hybridizes under high stringency conditions, which conditions are prehybridization and hybridization at 42° C. in 5× SSPE (1× SSPE is 150 mM sodium chloride, 10 mM sodium phosphate, 1 mM ethylenediaminetetraacetic acid, pH 7.4), 0.3% SDS (sodium dodecyl sulfate), 200 μg/ml sheared and denatured salmon sperm DNA, 50% formamide; and wash at 42° C. for 15 minutes in 2× SSC (1× SSC is 150 mM sodium chloride, 15 mM sodium citrate, pH 7.0), 15 minutes in 1× SSC, 1% SDS, and 15 minutes in 0.5× SSC, 0.1% SDS, with the nucleic acid sequence of SEQ ID NO:1 or SEQ ID NO:3.

2. The nucleic acid construct of claim 1, wherein the nucleic acid sequence encoding an SRP54 protein encodes an SRP54 protein having the amino acid sequence of SEQ ID NO:2.

3. The nucleic acid construct of claim 2, wherein the nucleic acid sequence encoding an SRP54 protein is SEQ ID NO:1.

4. The nucleic acid construct of claim 1, wherein the nucleic acid sequence encoding an SRP54 protein encodes an SRP54 protein having the amino acid sequence of SEQ ID NO:4.

5. The nucleic acid construct of claim 4, wherein the nucleic acid sequence encoding an SRP54 protein is SEQ ID NO:3.

6. The nucleic acid construct of claim 1, wherein the nucleic acid sequence encoding an SRP54 protein is contained in plasmid pShTh24 which is contained in *E. coli* NRRL B-21327.

7. The nucleic acid construct of claim 1, wherein the nucleic acid sequence obtained from an Aspergillus strain hybridizes under high stringency conditions, which conditions are prehybridization and hybridization at 42° C. in 5× SSPE, 0.3% SDS, 200 μg/ml sheared and denatured salmon sperm DNA, 50% formamide; and wash at 42° C. for 15 minutes in 2× SSC, 15 minutes in 1× SSC, 1% SDS, and 15 minutes in 0.5× SSC, 0.1% SDS, with the nucleic acid sequence of SEQ ID NO:1.

8. The nucleic acid construct of claim 7, wherein the Aspergillus strain is an *Aspergillus niger* strain.

9. The nucleic acid construct of claim 7, wherein the Aspergillus strain is an *Aspergillus oryzae* strain.

10. A recombinant vector comprising the nucleic acid construct of claim 1.

11. A recombinant host cell comprising one or more of the nucleic acid constructs of claim 1.

12. The cell of claim 11, which further comprises a nucleic acid sequence encoding a protein heterologous to the cell.

13. The cell of claim 11, which is a filamentous fungal cell.

14. The cell of claim 13, wherein the filamentous fungal cell is an Aspergillus cell.

15. A method for the recombinant production of a protein comprising culturing the host cell of claim 11 under conditions conducive for the production of the protein, wherein the cell produces larger amounts of the SRP54 protein than a wild type cell cultured under the same conditions and the cell contains a nucleic acid encoding the protein, and recovering the protein.

* * * * *